United States Patent [19]

Brauer et al.

[11] Patent Number: 4,486,179

[45] Date of Patent: Dec. 4, 1984

[54] BIOCOMPATIBLE CEMENTITIOUS DENTAL COMPOSITIONS

[75] Inventors: Gerhard M. Brauer, Bethesda; Jeffrey W. Stansbury, College Park, both of Md.

[73] Assignee: The United States of America as represented by the Secretary of the Department of Health and Human Services, Washington, D.C.

[21] Appl. No.: 582,759

[22] Filed: Feb. 23, 1984

[51] Int. Cl.$^3$ .............................................. A61K 6/08
[52] U.S. Cl. .................................... 433/199; 106/35; 260/998.11; 433/201; 433/202; 433/217; 433/228; 523/115; 523/116; 523/118; 524/291; 524/433
[58] Field of Search .................. 106/35; 523/115, 116, 523/118; 260/998.11; 433/199, 201, 202, 217, 228; 524/291, 433

[56] References Cited

U.S. PATENT DOCUMENTS 2,936,242  5/1960  Brauer ..................................... 106/35
3,509,089  4/1970  Dougherty ............................. 106/35
4,362,510  12/1982 Brauer et al. ......................... 433/199

*Primary Examiner*—Lorenzo B. Hayes
*Attorney, Agent, or Firm*—Browdy and Neimark

[57] ABSTRACT

Dental cements with syringate esters such as 2-ethylhexyl syringate with or without vanillate esters dissolved in o-ethoxybenzoic acid as ingredients of the liquid when mixed with metal oxide powder yield rapid setting, insoluble cements that have high strength, do not inhibit free radical polymerization, adhere strongly to metal, and reduce carries. Use of silanized glass filler to the powder in conjunction with the addition of monomer to the liquid gives an even stronger cement.

26 Claims, No Drawings

BIOCOMPATIBLE CEMENTITIOUS DENTAL COMPOSITIONS

FIELD OF INVENTION

The present invention relates to improvements in dental compositions, and, more particularly, to high strength cementitious materials suitable for use as luting agents, sedative and insulating bases, temporary and long term restoratives, endodontic sealants, pulp capping materials, soft tissue packs, impression pastes and adhesives for dental composites and hard tissues. Specifically, the present invention relates to highly biocompatible, high strength, low solubility, insulating bases and restoratives containing syringic acid esters dissolved in chelating agents and metal oxides that adhere to metals and resins.

The invention also relates to silanized glass-filled cementitious materials suitable as intermediate, semi-permanent restorative materials and as a restorative in the repair of fractured porcelain or porcelain to metal crowns and bridges.

BACKGROUND OF THE INVENTION

Oil of cloves has been used in the treatment of dental caries since the XVI century and its inclusion in combination with zinc oxide in dental cements, commonly referred to as luting agents, was reported over 100 years ago. Analysis revealed that oil of cloves contains approximately 85% by weight of eugenol. It is this latter compound which is used in zinc oxide-eugenol (hereinafter referred to as ZOE) dental cements. ZOE compositions have found wide application in dentistry including temporary restoratives, sedative bases, cementing media for crown and bridge work, in pulp capping, soft tissue packs in oral surgery and periodontics, root canal sealants in endodontics and with modifying agents as impression pastes.

ZOE cements possess much better biocompatibility than most other dental materials. They have excellent sealing characteristics and their bacteriocidal effectiveness has been well demonstrated. The cement acts as a palliative or anodyne and as a mild non-irritant antiseptic. Unfortunately, these materials have low strength, which are often insufficient to resist forces of mastication. Their lack of resistance to wear and disintegration, partially because of their high relative solubility in oral fluids of the mouth, further deters their more extensive use as temporary restorations or fillings. These materials also inhibit free radical polymerization because of the presence of an electron-rich phenolic hydroxyl group in the eugenol molecule. Thus, acrylic resins, and to a lesser extent composites, in contact with a ZOE cement do not polymerize completely. This incomplete cure results in polymer surface regions having poor physical properties such as low surface hardness. ZOE cements adhere only weakly to acrylic restorations, bone or dental tissues. Moreover, eugenol has shown no evidence of inhibiting caries formation.

Although the eugenol ingredient is relatively non-toxic ($LD_{50}$ of 0.5 g/kg for white mice), free eugenol has some inflammatory characteristics. Thus, when injected into the abdominal integument and eyes of rabbits, eugenol produces severe inflammation. It produces leucocytic infiltration and polymorphonuclear responses, and in direct contact with the pulp or periodontal tissue eugenol can act as a coagulent. In in vitro tests it shows a hemolyzing, protein precipitating action.

A further disadvantage is that eugenol has a penetrating long-lasting odor and lingering taste which is unpleasant to many patients. In addition, incompletely hardened cements containing much residual eugenol can produce irritation and toxic cell reactions.

To overcome some of these deficiencies, especially to improve the mechanical strength of the ZOE cement, research has been directed to either replacing eugenol altogether with a more suitable substitute or towards including additives in the ZOE compositions which alleviate some of the problems. However, the use of eugenol substitutes has often resulted in cements possessing poor physical properties.

Zinc oxide will react with many chelate forming compounds, especially those containing o-methoxy-phenol (guaiacol) groups to yield cementitious products. Cements obtained from o-ethoxybenzoic acid (referred to hereinafter as EBA) and zinc oxide have found a considerable number of applications in dentistry because of their strength and excellent biocompatibility, especially as luting agents and as bases. However, under clinical conditions the materials still disintegrate too rapidly to be employed for more permanent conditions.

Recently, Brauer, Argentar and Stansbury (U.S. Pat. No. 4,362,510; also see Brauer, G. M.; and Stansbury, J. W.; and Argentar, H.: Development of High-Strength, Acrylic Resin-compatible Adhesive Cements, J Dent Res 62, 366 (1983).) have developed cements comprising a liquid made up of vanillic ester such as n-hexyl vanillate, a chelating agent and a zinc oxide-aluminum oxide and hydrogenated rosin powder. Vanillate esters such as n-hexyl vanillate (HV) dissolved in o-ethoxybenzoic acid react with zinc oxide powders to yield high-strength, adhesive cements, which are much less soluble than ZOE cements, do not inhibit polymerization of acrylic monomers and can be formulated with them. Such cements, with or without the resin or polymer, have excellent strength and adhere well to non-precious metal, resins and porcelain. However, n-hexyl vanillate has shown no evidence of inhibiting caries formation.

Syringic acid (3,5-dimethoxy-4-hydroxybenzoic acid) has a molecular structure somewhat similar to vanillic acid with an additional methoxy group in the "5" position of the aromatic ring. The acid, when used as a feed additive for rats, has shown a larger reduction in caries of the rats than any other phenolic compounds and amino acids studied (Thompson, Vogel and Phillips, J. Dent Res 44:596–599, 1965). Other phenolic compounds such as eugenol as well as amino acids did not inhibit caries formation at the level tested.

Various phenols including vanillin and syringic acid have been tested for their inhibitory effects on the polymerization of methyl methacrylate (Chem. Abstracts 83: 179694t, 1975), the tested phenols having activities lying between the extremes produced by hydroquinone and vanillin.

Intermediate restorations are commonly used in dentistry, especially in pedodontics. Often for patients with rampant caries, gross cavities should be repaired expeditiously to alter the oral flora and arrest the caries process. When this has been accomplished permanent restorations can be placed. Removal of the caries until completion of the restorative work may take several months or longer. An intermediate restorative is used during this time to protect the teeth and should have a useful service life of from 1 to 3 years. ZOE type cements, because of their excellent biocompatibility, have been until now the material of choice for this type of restoration. Some commercial brands use a powder composed of zinc oxide and from 20 to 40% of finely divided polymer particles to improve toughness and abrasion resistance. However, as noted above, the ZOE type cements are not sufficiently strong.

SUMMARY

It is, accordingly, an object of the invention to overcome deficiencies in the prior art such as indicated above, and to promote dental health.

It is another object to provide for improved dental materials, especially to provide improved dental cements.

It is a further object to provide an improved dental cement which has various dental uses and has high strength, good biocompatibility and anti-caries activity.

In accordance with the invention, incorporation of syringic acid esters into dental compositions, such as those based on zinc oxide, in place of all or a substantial amount of vanillic esters, is found to provide the above objectives.

Thus, on reacting low melting syringate esters, such as 2-ethylhexyl syringate, preferably together with n-hexyl vanillate (HV), in a suitable liquid chelating agent reactable with zinc oxide, e.g. o-ethoxybenzoic acid (EBA), with zinc oxide powders, there are obtained insoluble high strength cements which do not inhibit polymerization of acrylic and methacrylic monomers. The cements so obtained have much stronger adhesion to composites and non-precious metals than ZOE cements. Because of the caries reducing syringate ingredient, such cement possess excellent biocompatible properties, making them most useful as insulating bases, pulp capping agents, root canal sealers, soft tissue packs or as intermediate-restoratives.

In another aspect, the present invention relates to the use of vanillate-EBA and syringate-vanillate-EBA cements containing silanized glass as a strengthening agent, which cements are suitable as intermediate restorative resins and restoratives in the repair of fractured porcelain or porcelain to metal crown and bridges.

In this latter aspect of the present invention, advantage is taken of the unique behavior of the HV-EBA liquid component in not inhibiting polymerization. This makes it possible to add monomers such as mono- or dimethacrylates to the liquid. In the presence of suitable initiator-accelerator systems these monomers will polymerize during the cement cure. Thus, with the appropriate amine accelerator added to the modified liquid composition and with benzoyl peroxide or other suitable peroxide initiator incorporated into the powder the monomer polymerizes. Furthermore, silanized glass reinforcing agent added to the powder synergistically cooperates with the other ingredients and improves the strength of the resulting "cement-composite".

The present invention thus relates to various high-strength cementitious dental compositions which contain substantially no eugenol, more especially to (1) metal oxide-chelate compositions containing silanized glass and one or more chelating compounds at least one of which is an ester of vanillic acid or its isomers or an ester of syringic acid and (2) similar compositions without silanized glass, but containing a syringic acid ester, which compositions (1) and (2), because of the absence of eugenol or like materials, do not inhibit polymerization of monomeric materials commonly used in an oral environment, such as acrylates and methacrylates.

The compositions may contain other additives such as a rosin, a second metal oxide, polymeric materials and one or more acidic materials to impart various desirable properties to the composition both before and after curing. The cementitious materials herein described, when cured, adhere strongly to non-precious metals, amalgams, acrylic resins and composites even after prolonged exposure of the adhesive joint or interface to an aqueous environment.

The present invention also contemplates the inclusion of cross-linking agent which thereby provide compositions suitable for use as dental restoration or filling materials. Such materials include di-and polyvanillate esters and monomers which generally polymerize by a free radical mechanism.

DETAILED DESCRIPTION OF EMBODIMENTS

The present invention is directed to cementitious dental compositions which provide ease of manipulation and handling in a variety of dental applications. When set, these materials are compatible with, and will not inhibit curing of, polymerizable materials of the type generally used in an oral environment, such as the acrylates and methacrylates. The compositions, when cured, provide high strength, low solubility in an oral environment, high biocompatibility and high adhesion to acrylic, metal and porcelain surfaces.

The desired ease of manipulation and handling as well as the required properties of the cured material are obtained by mixing, immediately before use, a solid phase containing one or more metal oxides in powder form with a liquid phase containing one or more chelating agents.

Metal oxides which are suitable for use in the present invention are the oxides of metals found in Groups IIA and IIB of the periodic table as well as tin oxide (Group IVB). Metal oxides as used herein would also include the oxides and hydroxides of these same metals. The oxides and hydroxides of zinc, calcium, tin, barium and magnesium are preferred, and zinc oxide is the most preferred of the metal oxides.

The compounds of the present invention which form the desired chelates with the metal oxides are esters of syringic acid, preferably in combination with esters of vanillic acid. In those embodiments for use as restoratives, and incorporating silanized glass as a reinforcing agent, vanillic acid ester may replace the syringic acid ester entirely, without of course providing the beneficial anti-caries activity of the syringic acid ester.

Syringic acid esters preferred as ingredients of dental cements are solids at room temperature. Most preferred in the 2-ethylhexyl ester which is a low melting solid with apparent plasticizing action. Dissolved in o-ethoxybenzoic acid (EBA) or other liquid chelating agent such as guaiacol, it yields a liquid that easily mixes with zinc oxide powders. Depending on the powder-liquid ratio employed, compositions with varying physical properties desirable for different dental applications can be prepared.

Syringate ester containing materials, especially those made from mixtures of 2-ethylhexyl syringate (EHS), hexyl vanillate (HV) and (EBA) have characteristics similar to HV-EBA cements. Compared to the commonly used ZOE materials they have improved strength, low solubility, do not inhibit polymerization and are compatible with acrylic monomers. They also bond well to resins, non-precious metals and porcelain, the bond strength being much higher than values for ZOE luting agents. The results of measurements of hexyl syringate (HS) and EHS-EBA cements passed, and usually exceeded greatly, the requirements of Type II Class 1 (cements for permanent cementation purposes), Type III, Class 1 (filling material and bases) and Type IV (cavity liners) of ADA Specification No. 30 for Dental Zinc Oxide-Eugenol Type Restorative Materials.

Analogous to HV-EBA cements (see U.S. Pat. No. 4,362,510), non-toxic monomers and reinforcing fillers can be incorporated into syringate compositions (also see Brauer, G. M.; and Stansbury, J. W.: Cements Containing Vanillate Esters, EBA and Zinc Oxide, *J Dent Res* 61:331 (No 1377), 1982). The resultant compositions have low solubility and high strength, finding applications as durable intermediate restoratives. However, a main advantage of these materials is their improved biocompatibility; thus, while HV-EBA cements have pulp reactions that are similar to or even milder than those of commercial ZOE cement, the additional methoxy group on the ring as well as the ethyl group in the ester side chain of EHS further raise the molecular weight, thereby lowering its diffusion into the pulp relative to HV.

The other main advantage concerns the caries reducing characteristics of syringic acid and its derivative esters. Thus, the use of the syringic acid esters, optionally in conjunction with fluoride which can be readily incorporated into the cement, yields a material with very desirable anti-caries characteristics. It should be understood that the concentration of syringate in the cement must be sufficient to cause anti-caries activity in the syringate-zinc oxide reaction product.

The vanillic acid compounds in the present invention include esters of vanillic acid (4-hydroxy-3-methoxybenzoic acid) or its isomers, as for example isovanillic acid (3-hydroxy-4-methoxybenzoic acid) or o-vanillic acid (2-hydroxy-3-methoxybenzoid acid), or homologs as for example homovanillic acid which are liquids at or within 30° C. above room temperature. The esters of the latter compound in high concentration may be somewhat inhibiting. Vanillic acid, itself a solid, may be used in the present invention.

The esters of vanillic acid and its isomers suitable for use in the present invention include those compounds in which the alcoholic radical results in the ester being a liquid at a temperature of approximately 55° C. Such groups include saturated, unsaturated, branched and straight chain alkyl groups. Arylalkyl groups are also suitable when they result in a liquid ester at or within 30° C. of room temperature. Also suitable di-and polyvanillate esters of polyfunctional radicals, such as may be derived from glycols and polyhydric compounds. The preferred alkyl vanillates are those having a straight or branched chain alkyl group having between 4 and 15 carbon atoms. When the alkyl group is a straight chain radical, between 5 and 12 carbon atoms is preferred, with hexyl vanillate being most preferred. Replacing hexyl vanillate with other esters of vanillic acid yield cements with properties similar to those employing hexyl vanillate. However, these cements may possess specific properties such as increased hydrophobicity which makes the hardened material more desirable for specific applications in dentistry where water repellancy and minimum solubility of the material in the mouth's fluids is of prime importance.

As indicated above, isomers of vanillic acid may be used when they result in an ester which is a liquid at or within 30° C. of ambient temperature. The preferred isomers are those having the methoxy and hydroxy groups in adjacent or ortho positions to each other. The most preferred isomers are o-vanillic and isovanillic esters. Homologs of vanillic acid and its isomers are also suitable, as for example homovanillic acid or the acids in which an ethoxy group has been substituted for a methoxy group.

As noted above, a liquid chelating agent such as EBA should also be present in the composition. By including such a liquid chelating agent, hardening is accelerated. Suitable solvent-chelating agents include those compounds which are liquid and contain groups capable of chelating or reacting with the metal oxide like the vanillate and syringate esters, forming a ring in which the metal ion is at the center of a coordination complex. These compounds should also be able to dissolve the vanillate or syringate ester. Appropriate solvent-chelating compounds should also lack polymerization inhibiting groups. Preferred compounds would include o-ethoxybenzoic acid (EBA), ethoxyacetic acid, lactic acid, salicylaldehyde, 2-propoxy-5-methylbenzoic acid and, if non-inhibition of polymerization is less important than strength, alkoxyphenols, generally. The preferred compound is EBA which has demonstrated efficacy in similar cementitious compositions for certain types of dental applications.

Further reductions in setting time may be achieved by addition of small amounts of acid to the liquid or powder phase prior to mixing. Although a mineral acid may be employed, organic acids, particularly carboxylic acids, prove quite effective. Preferred acids would include acetic, propionic acrylic acid, methacrylic acid, polyacrylic acid, benzoic acid, hydrocinnamic acid and polycarboxylated polystyrene. A substance which is both a carboxylic acid and capable of forming a chelate with a metal oxide is frequently preferred, depending upon other variables related to the interactions with other components and their concentrations in the mixture as well as the ultimate application of the cementitious material. Many of the compounds indicated above as preferred chelating compounds serve both purposes. In addition, dimethylolpropionic acid has proven quite effective in this dual capacity.

As noted above, a preferred composition may contain several other components in the powder phase. A reinforcing agent of the type commonly used in such compositions may be added to improve compressive strength and lower film thickness. Fused quartz, glass, silica and aluminum oxide are examples of suitable reinforcing agents with $Al_2O_3$ having particle sizes between $0.5\mu$ to $20\mu$ being especially acceptable. The concentration of the latter being preferably in the range of 0–50%, based on the weight of the solid phase, and most preferably 30% by weight.

Especially preferred, however, is the use of silanized glass powder as the reinforcing agent either by itself or, preferably, in admixture with other reinforcing materials such as $Al_2O_3$. Thus, a composition containing about 10% alumina and about 33% silanized glass (exclusive of the monomer) gave, upon curing, intermediate restorative cement composites having excellent compressive and tensile strengths. Silanization of other fillers did not improve the strengths.

Rosin, rosin esters or abietic acid (the major constituent) of rosin may be added to improve consistency such as lower film thicknesses and smoother mixing characteristics. Unfortunately, these materials also increase solubility and decrease the strength of the cured composition. Hydrogenated rosin, of the type sold under the name of STAYBELITE (trademark of Hercules, Inc., Wilmington, Del.), not only improves mixing characteristics but also reduces solubility and disintegration. Compressive strength varies inversely with the amount of hydrogenated resin added, but at low concentrations (below 2%) with fine ZnO particles, tends to increase the compressive strength beyond that which would occur in its absence. Hydrogenated rosin also is stable to oxidation and yields cements with good color stability. In determining the appropriate quantitative composition, the properties of ease of manipulation, curing time, hardness, solubility, adhesion and strength must be carefully considered since variation both in type and amounts may influence more than one of these properties. However, the preferred amount of hydrogenated rosin which achieves the optimum balance of these properties is in the range of 1.5 to 15% by weight of the solid phase; 6% by weight being the most preferred concentration.

Although the preferred powder or solid phase of the present invention comprises, by weight, 40 to 98.5% ZnO, 0 to 40% $Al_2O_3$, 0 to 55% silanized glass powder and 1.5 to 15% hydrogenated rosin and the solid phase composition which is most preferred is 32% ZnO, 15% $Al_2O_3$, 50% silanized glass and 3% hydrogenated rosin, other substances may be substituted in part for the constituents.

Because of the electron poor nature of the hydroxyl group of the vanillates and syringates neither of these types of compounds nor their composition with EBA inhibits polymerization of acrylic resins or composites. On the other hand, the inhibiting action of the commonly used materials, eugenol, or 2,5-dimethoxyphenol, when added in small amounts to the catalyst paste of a commercial composite demonstrates inhibition of polymerization.

Not only is the rate of polymerization of resin that is contacted unchanged when using the newly developed cement, but also the surface properties of composites cured against the newly hardened cement remain unaltered.

The present cements adhere strongly to non-precious dental alloys and to amalgams, dental resins and composites. Non-precious alloy, disks or rods, when cemented together with the cements and placed in water also adhere strongly. Even after 12 months storage of the specimens in water, this bonding is still extremely strong. Similarly, cement disks cured against dental composite have strong adhesion to the composite after 12 months storage in water. Cements based on ZOE or EBA do not bond to such substrates to any appreciable extent.

The complete absence of inhibition of the present cements, coupled with their excellent adhesion to resins, porcelain and metals and their substantial compressive and tensile strength renders these materials highly desirable in applications for which ZOE cements are unsuitable. Thus, acrylic resins or composites may be placed over bases formed from the cement. A portion of the cement, when used clinically as a temporary restoration, or filling, may be retained as a base for an acrylic resin restoration. This avoids the procedure of completely reexposing deep cavities, thus further reducing irritation of the dental tissues.

As the present cementitious compositions adhere extremely well to many polymeric materials, temporary restorations which incorporate polymers as reinforcing materials in the cements themselves are effective for such purposes. The polymers may be added to either the liquid or the powder depending upon the solubility of the polymeric material in the liquid phase. Rubbery polymers, for instance, may be dissolved in the liquid; whereas solid polymers of small particle sizes (i.e. sizes comparable to those of the ZnO, silanized glass and $Al_2O_3$) may be incorporated in the powder.

A variety of polymeric materials may be used including polyacrylates and methacrylates (derived from the corresponding monomers of the free acids and their alkyl esters); vinyl polymers including poly(vinyl acrylates) and methacrylates; poly(vinyl chloride); poly(vinyl acetate); polystyrene; polyacetal; polyurethanes; polycarbonates and various copolymers such as butadiene-acrylonitrile copolymers; acrylonitrile-butadiene-styrene terpolymers and vinyl chloride-vinyl acetate copolymers, as well as mixtures of the foregoing. Where high stress-bearing cements are sought, the poly(alkyl acrylates) and poly(alkyl methacrylates) are preferred, poly(methyl methacrylate) being most preferred. The polymeric material may be incorporated into the cement in amounts between 1 and 20% by weight of the total composition and preferably between 2 and 10%.

With different powder to liquid (P/L) ratios, compositions having varying physical properties, useful for different dental applications, can be prepared. Depending on the consistency, mixing characteristics and film thickness desired for specific applications, the materials are useful as intermediate restoratives, insulating bases, root canal restorations and as pulp capping and luting agents.

Generally, the larger the amount of powder incorporated per unit volume of liquid the greater is the strength and the lower the water solubility. Too high a P/L ratio yields mixes of high consistency, which, because of poor handling characteristics, would not be suitable for clinical applications. Inclusive of all possible applications, the preferred range is 0.9–2.9 g powder/0.2 ml liquid, preferably 1.0–2.4 g of powder/0.2 ml.

The powder-liquid ratio to be employed depends on the ultimate use of the cement. Thus, a material prepared by mixing 1.1 g to 1.3 g of powder with 0.2 ml liquid is suitable as a luting agent for cementation of crowns and bridges where a material having a thin film thickness is preferred. Mixes of heavier consistency are useful as insulating bases, and with or without modifications, as materials for temporary fillings. Other uses of these materials are as pulp capping agents, root canal restorations and, with modifications, as impression pastes. The material properties surpass the requirements of American Dental Association Specification No. 30 for Dental Zinc Oxide-Eugenol Type Restorative Materials, Type III, Class 1 (filling materials and bases), and Type IV (cavity liners). If the powder components are sieved to give a proper film thickness in the hardened cement, these materials will significantly exceed the requirements of Type II, Class 1 cements (for permanent cementing purposes).

The superior physical and chemical properties described above may be obtained by another variant, i.e.

an ester cross-linking agent. In the case of the alkyl vanillates or most chelating compounds, it is generally accepted that a single divalent metal ion is capable of complexing two molecules of chelating compound as an independent unit. However, when the organic molecule contains two or more vanilate groups as extended network can occur since each organic molecule contains two or more "chelating" sites capable of reacting with a metal ion. Such di- or polyvanillates which are suitable for use in the present invention may be prepared by reaction of vanillic acid or its isomers with a suitable polyhydric compound such as a glycol, according to a standard esterification reaction as that outlined below. As in the case of the monovanillates, the suitability of the polyhydric compound is determined by its overall effect on the physical state of the resultant polyvanillate, a liquid at temperatures of about 55° C. or below being one of the prime requirements. Thus, for preparing di- and polyvanillate esters, branched, straight chain and cyclic polyols and α, ω-glycols may be used, having from about 4 to 15 carbons atoms, with those having 5 to 12 carbon atoms preferred. The di- and polyvanillate esters may be used in addition to or substituted in whole or in part for monoalkyl esters described heretofore. Low melting solid and liquid polyalkylene glycols may also be used as for example polyethylene glycols such as the Carbowaxes or PEG with molecular weights below approximately 2000.

In view of the absence of any inhibitory effect on free radical polymerization and the strong adhesion of the cementitious compositions described above, other vanillate compositions may be formulated which additionally contain polymerizable groups. These monomer containing compositions, because of their superior mechanical properties, particularly their compressive and tensile strengths, may be employed as restoratives.

Suitable monomers include those which polymerize by a free radical mechanism, preferred being those containing one or more acrylate, methacrylate or vinyl groups. Particularly preferred are those compounds which cure by a redox initiator-accelerator mechanism or by irradiation. Examples of such preferred compounds include alkyl acrylates and methacrylates, such as methyl and ethyl acrylate and methacrylate, alkylene glycol diacrylates and dimethacrylates in which the alkylene group contains 2 to 12 carbon atoms and polyol polyacrylates and polymethacrylates in which the polyol contains 2 to 12 carbon atoms and the number of acrylate or methacrylate moieties per polyol radical is between 2 to 6. The monomer is mixed with the liquid in the range of 2.5 to 75% by weight, based on the weight of the liquid phase, preferably 5 to 60%.

Any compound capable of initiating polymerization of such monomers is suitable, particularly peroxides, such as benzoyl or lauryl peroxide, or the methyl ether of benzoin. The initiator is used in concentrations of approximately 0.5 to 2% by weight, based on the weight of the liquid phase.

Compounds which are conventionally used to accelerate such polymerization reactions may be employed in this embodiment. Amines, particularly tertiary amines, are quite suitable if diacyl peroxide is the initiator, and a discussion of those which may be used in this type of reaction are described by Brauer et al., in "4-N,N-Dialkylaminophenethanols, Alkanoic Acids and Esters: New Accelerators for Dental Composites", JOURNAL OF DENTAL RESEARCH, Volume 60, pp. 1343-1348, July 1981. The preferred compounds include dihydroxyethyl-p-toluidine, p-(dimethylamino)-phenethanol and p-(diethylamino)phenylacetic ethyl ester. Based on the weight of the monomer, the accelerator should be present in concentrations of approximately 0.5 to 2.0%, by weight.

If free radical polymerizable monomers are present, to extend storage stability, a trace amount of an inhibitor may be added to the liquid.

When compositions containing monomers are employed, reinforcing fillers may be added in amounts of up to 80% by weight of the solid phase to improve mechanical strength. Glass or silica of the type generally employed in the formulation of conventional dental composite resins are acceptable. Preferably, the glass fillers are silanized and all fillers coated with initiator by conventional techniques.

The following examples provide details of the manner and mode of making and using various embodiments of the present invention. Neither these examples nor any of the foregoing disclosure should be construed as limiting in any way the scope of the present invention.

EXAMPLE 1

Synthesis of n-hexyl syringate (HS):

To 9.91 g (0.05 mol) of syringic acid was added 10.22 g (0.10 mol) of dried hexanol, 0.1 g p-toluenesulfonic acid and 25 ml cyclohexanone to dissolve the acid. The mixture was refluxed for 10 h. Since considerable unreacted syringic acid remained, more hexanol (0.1 mol) was added along with 0.1 g p-toluenesulfonic acid and cyclohexanone, and refluxing was continued for an additional 24 h. Solvent was removed by distillation. The residue was taken up in $CH_2Cl_2$ and extracted successively with aqueous $NaHCO_3$ and $H_2O$. On distilling the organic phase, a red liquid boiling at 190°–220° C./4–5×10$^2$ Pa was obtained which crystallized on cooling.

Infrared spectrum of the solid indicated that this was a mixture of syringic acid with hexyl syringate. Further purification of the $CH_2Cl_2$ solution by repeated extraction with 5% $NaHCO_3$, $H_2O$, each saturated with $CaCl_2$, removal of the solvent and recrystallization from n-hexane yielded very pale yellow crystals MP=62.5° C. The yield was 4.2 g, 30%. Calculated for $C_{15}H_{20}O_5$ the elemental analysis was: C, 63.81%; H, 7.85%; it was found that: C, 64.00%; H, 7.95%.

EXAMPLE 2

Synthesis of 2-ethylhexyl syringate (EHS):

To 13.2 g (0.1 mol) 2-ethyl-1-hexanol in a flask equipped with reflux condenser connected to a Dean-Stark trap was added 9.9 g (0.05 mol) syringic acid, 0.2 g p-toluenesulfonic acid and 75 ml toluene. The mixture was refluxed for 20 h. Excess alcohol and toluene were distilled off under slight vacuum. The dark liquid residue was diluted with $CH_2Cl_2$ and extracted with 2% $NaHCO_3$+15% aqueous NaCl followed by neutral 15% aqueous NaCl solution. The organic layer was dried with anhydrous $Na_2SO_4$ and distilled. After removal of all unreacted 2-ethylhexanol the product distilled over as a viscous, colorless liquid, b.p. 204°–209° C./4×10$^2$ Pa, which crystallized on standing at room temperature to a fine white solid, mp 35°–36° C. Yield: 10.1 g, 65%.

EXAMPLE 3

All chemicals used were reagent grade except n-hexyl vanillate which was synthesized as described by Brauer et al (*J. Dent Res.* 62).

A number of commercial dental materials, i.e. composite ("Adaptic", Johnson and Johnson, East Windsor, N.J.), ZOE cement ("Fynal", L. D. Caulk Co., Milford, DE.), and nickel-chrome alloy ("Pentillium", Pentron Corp., Wallingford, CT.) were employed to determine their bond strength to cements.

The cement powder was prepared in a V-shaped blender from 64% zinc oxide (sieved through a No. 70 sieve); 30 g of aluminum oxide (Alumina T-61 for the n-hexyl syringate containing cement and Alumina T-61-325 for the 2-ethylhexyl containing cement, Aluminum Company of America, Bauxite, AR.) pretreated by heating four h to 700° C., followed by cooling and then sieving through a No. 270 mesh sieve; and 6 g of hydrogenated rosin (passed through a No. 100 sieve). Consistency, setting time, compressive strength, and solubility and disintegration were determined according to the respective tests of ANSI/ADA Specification No. 30 for Dental Zinc Oxide-Eugenol Type Restrorative Materials. The diametral tensile strength was measured with a universal testing machine at a loading rate of 0.5 cm/min.

The bond strength of vanillate cements to composites and non-precious metals were measured quantitatively by a modification of the procedure of Lee, et al *J Dent Res* 48:211-216, 1969).

The thoroughly mixed cement was placed in the recessed tip of a stainless steel cylinder and was covered with a polyethylene sheet. To smooth the surface a glass slab was pressed against the sheet. Three minutes after starting the mix the sheet was removed from the cylinder, the cement was placed against the metal surface which had previously been polished with a No. 600 grit carbide paper. A 3 kg load was then placed on top of the cylinder for 15 sec. The assembly, after storage for 1 h in a 37° C.-100% relative humidity bath, was kept in 37° C. water for an additional 23 h prior to placing it in a universal testing machine. The tensile strength of the cement-metal bond of 5 specimens was determined at a loading rate of 0.5 cm/min.

To determine the strength of the cement-composite bond, the covered cement specimens were placed in a 37° C. bath kept at 100% relative humidity 3 min. after initiating the mix. Eight min after starting the cement mix a composite was spatulated and packed into a tapered mold (smaller diameter facing up) that had been coated with 3% polycrystalline wax in toluene as release agent. The cylinder containing the cement was removed from the bath 9.5 min after initiating the mix. The polyethylene sheet and any remaining flash was removed. After 10 min the cement end of the cylinder was placed against the composite. A 3 kg load was placed on the cylinder for 15 sec. The tapered mold was stored in the 37° C. bath for 1 h and then in water for 23 h prior to placing the assembly into a universal testing machine. The tensile strength was determined as previously described.

Hexyl syringate (HS) and 2-ethylhexyl syringate (EHS) are solids at room temperature. Solutions of these compounds were dissolved in EBA, in which they are readily soluble, and mixed with 64.0% zinc oxide, 30.0% aluminum oxide and 6.0% hydrogenated rosin powder. Liquids with 3% to 14% HS, 0 to 10% hexyl vanillate (HV) and 86% to 93% e-ethoxybenzoic acid (EBA) as well as compositions with 5% to 10% EHV, 0 to 7% HV and 88% to 89.5% EBA were prepared. In Table 1 and Table 2 are given the compositions, setting times, strength and solubilities of cements containing HS and EHS respectively.

TABLE I

Properties of Cements Containing n-Hexyl Syringate (HS)
Powder: 64% ZnO - 30% $Al_2O_3$ - 6% Hydrogenated Rosin
Powder/Liquid Ratio: 1.3 g/0.2 (luting consistency)

| Composition of Liquid, % | | | Setting | Strength, MPa* | |
|---|---|---|---|---|---|
| n-Hexyl Syringate | n-Hexyl Vanillate | EBA (%) | Time (min.) | Compressive | Tensile |
| — | 12.5 | 87.5 | 5.5 | 61.4 (11.2) | 5.0 (0.1) |
| 7 | — | 93 | 4 | 54.4 (12.0)* | — |
| 10.5 | — | 89.5 | 4 | 62.2 (10.8) | 5.5 (1.4) |
| 14 | — | 86 | 4 | 59.2 (5.7) | — |
| 5 | 8 | 87 | 4.5 | 42.9 (6.0) | 7.5 (1.2) |
| 3 | 10 | 87 | 8 | 37.7 (12.0) | 6.1 (0.3) |

*Means of 5 determinations (standard deviation).

At luting consistency, mixes containing HS hardened rapidly, usually in 4 to 4.5 min. Their compressive and tensile strength was high and ranged from 54 to 62 MPa and 5.5 MPa respectively (Table 1). These values are similar to those of hexyl vanillate-EBA cements, but much higher than ZOE cements. Compositions with 3 to 5% n-hexyl syringate, 8 to 10% n-hexyl vanillate and 87% EBA as liquid had lower compressive strength (38-43 MPa), but higher tensile strength (6.1 to 7.5 MPa).

TABLE II

Properties of Cements Containing 2-Ethylhexyl Syringate (EHS)
Powder: 64% ZnO - 30% $Al_2O_3$ - 6% Hydrogenated Rosin

| Composition of Liquid, % | | | Powder g/0.2 mL Liquid** | Setting Time (min) | Strength, MPa* | | Solubility % |
|---|---|---|---|---|---|---|---|
| 2-Ethylhexyl Syringate | n-Hexyl Vanillate | EBA | | | Compressive | Tensile | |
| 10.5 | — | 89.5 | 1.0** | 9.5 | — | — | — |
| 10.5 | — | 89.5# | 1.0++ | 7 | 40.3 (0.7) | 5.7 (0.3) | — |
| 10.5 | — | 89.5# | 1.8 | 6 | 49.7 (12.5) | 5.2 (0.8) | — |
| 5 | 7 | 88 | 2.2 | 7 | 66.3 (3.4) | 6.0 (0.7) | 0.26 |
| 5 | 7 | 88 | 2.6++ | 7 | 66.7 (13.7) | 6.8 (1.3) | 0.44 |
| — | 12.5 | 87.5 | 1.3 | 5.5 | 61.4 (11.2) | 5.0 (0.1) | 0.47 |

TABLE II-continued

Properties of Cements Containing 2-Ethylhexyl Syringate (EHS)
Powder: 64% ZnO - 30% Al₂O₃ - 6% Hydrogenated Rosin

| Composition of Liquid, % | | | Powder | | Strength, MPa* | | Solubility |
|---|---|---|---|---|---|---|---|
| 2-Ethylhexyl Syringate | n-Hexyl Vanillate | EBA | g/0.2 mL Liquid** | Setting Time (min) | Compressive | Tensile | % |
| — | 12.5 | 87.5 | 1.7++ | 6.5 | 83.6 (11.0) | 6.2 (0.8) | — |

*Mean of 5 determinations (standard deviation)
0.1% acetic acid added
**Luting consistency
++Filling consistency
+⁼Aluminum oxide used was T-61

The hexyl syringate cements were quite brittle. To reduce fracture 2-ethylhexyl syringate, i.e., an ester with a side chain in the alcohol group, was synthesized. This is a compound with a much lower melting point than ES which may act as a plasticizing agent in the cured material. Cements with 10.5% EHS and 89.5% EBA had adequate strength (compressive strength 40 to 50 MPa, tensile strength 5.2 to 5.7 MPa, compared to most ZOE cements which have compressive strength of 16-38 MPa, tensile strength 1.4 to 2.5 MPa). Much better mechanical properties (compressive strength 66 MPa, tensile strength 6 to 7 MPa) and low solubility (0.26% to 0.47%) were obtained from liquids containing 5% EHS, 7% HV and 88% EBA. Such cements hardened rapidly, especially in the presence of small concentrations of acetic acid. On raising the powder/liquid ratio above that of a mix suitable as luting agent, the strength of the cement increased.

Addition of 1% of the liquid ingredient of the cement to a paste-paste composite did not inhibit its cure. Furthermore, in contact with the hardened cement a composite mix polymerized fully.

Results of measurements of the bond strength of various cements to selected substrates are given in Table 3.

TABLE III

Bond Strength of Luting Cements After Storage in Water for 24 Hours

| Bond | Bond Strength MPa | Bond Failure |
|---|---|---|
| ZOE to | | |
| Composite | 0.3 (0.5) | Adhesive |
| Stainless steel | 0.6 (0.8) | Adhesive |
| Hexyl vanillate (12.5%) - EBA (87.5%) to | | |
| Composite | 5.5 (2.6) | Cohesive |
| Stainless steel | 4.1 (0.9) | Cohesive |
| Nickel-chrome | 4.8 (1.0) | Cohesive |
| Ethylhexyl syringate (10.5%) - EBA (89.5%) to | | |
| Composite | 1.0 (0.8) | Mixed |
| Stainless Steel | 2.1 (1.2) | Cohesive |
| Ethylhexyl syringate (5%)-hexyl vanillate (7%) - EBA (88%) to | | |
| Composite | 1.5 (1.8) | Mixed |
| Stainless steel | 6.3 (0.9) | Cohesive |

Mean of all five measurements and standard deviation

The HV-EBA cements bond strongly to composites, non-precious metal and porcelain (4.1 to 5.5 MPa); the HS cement also adheres significantly to these substrates (1.0 MPa to 2.1 MPa). In comparison, the EHS-HV-EBA had excellent adhesion to stainless steel (6.3 MPa), but considerably less bonding to composite (1.5 MPa). All HV-EBA and the stainless steel EHS-HV-EBA bonds ruptured cohesively within the cement. Only very weak bonding (0.3 MPa to 0.6 MPa) takes place between ZOE and such substrates and bond failure occurred adhesively.

EXAMPLE 4

Zinc oxide is added to a 2% by weight solution of propionic acid in hexane. The slurry is mixed on a rotary evaporator for two hours, then heat and vacuum are applied to remove the hexane. The treated zinc oxide (or a portion of it) is added to Al₂O₃ and hydrogenated resin and mixed in the usual manner. The wetting of the zinc oxide powder with the propionic acid (or other acid, such as stearic acid) greatly speeds up the hardening of the syringate cement. Addition of propionic acid reduces brittleness and thus allows incorporation of higher concentrations of n-hexyl vanillate into the clinically useful cement.

In addition to the various additives outlined above, other additives may also be incorporated in the present cement compositions. Thus, small quantities of fluoride salts may be used. Plasticizers such as 10% zinc undecylate may be added to the cement powder, the resulting composition being useful as a tissue pack or whenever a flexible water-repellent coating is desired. In addition, the cement compositions may also contain ingredients such as antibiotics, and/or compounds to improve healing or to reduce plaque or gingivitis such as chlorohexidine.

Syringic acid esters useful as ingredients of dental cements are solids at room temperature. Most promising of those tested as an ingredient of cements is the 2-ethylhexyl ester which is a low melting solid with apparent plasticizing action. Dissolved in EBA it yields a liquid that easily mixes with zinc oxide powders. Depending on the powder/liquid ratio employed, compositions with varying physical properties desirable for different dental applications can be prepared. Syringate ester containing materials, especially those containing quantities of EHS, HV and EBA, have characteristics similar to HV-EBA cements. Compared to the commonly used ZOE materials they have improved strength, low solubility, do not inhibit polymerization and are compatible with acrylic monomers. They also bond significantly to resins and non-precious metals. The bond strength of EHS cements is somewhat less than that of HV-EBA cement, but much higher than values for ZOE luting agents; but this reduced strength is largely overcome by the inclusion of HV. The results of measurements of HS and EHS-EBA cements passed, and usually exceeded greatly, the requirements of Type II class I (cements for permanent cementation purposes), Type III, Class 1 (filling material and bases) and Type IV (cavity liners) of ADA Specification No. 30 for Dental Zinc Oxide-Eugenol Type Restorative Materials. Analogous to HV-EBA cements, monomers and reinforcing fillers can be incorporated into syringate compositions as noted above. Such materials should have low solubility and high strength and may find applications as durable intermediate restoratives. However, the main advantage of these cements is their improved biocompatibility. As the HV-EBA cements produce pulp reactions that are similar to or even milder than those of a commercial ZOE cement, the additional methoxy group on the ring as well as the ethyl group in the ester side chain of EHS further raise the molecular weight and reduce its diffusion into the pulp to a lower value than that of HV.

The caries reducing characteristics of syringic acid and its derivative esters studied, possibly in conjunction with fluoride which can be readily incorporated into the cement, yield a material with very desirable biocompatible characteristics.

Especially with regard to those embodiments of the present invention reinforced by silanized glass, it has been found that certain adjuvants are preferred. In general, besides the vanillate ester, the syringate ester if desired for its carries reducing activity, and the EBA, the liquid part of the composition should comprise an inhibited methacrylate monomer. The powder portion is made up of zinc oxide, aluminum oxide, a hydrogenated rosin and is reinforced by the silanized glass and a suitable initiator-accelerator system such as benzoyl peroxide-tertiary amine. The accelerator is one which is soluble in inhibited vanillate-EBA-monomer solutions and imparts good storage stability to such solutions. Examples of tertiary amines that do not yield premature polymerization of the liquid (and result in cured materials with minimum color) are N,N-dihydroxyethyl-p-toluidine and N,N-dihydroxyethyl-3,5-ditertiary-butylaniline.

Monomers comprising a high molecular weight compound of low volatility which are useful are: dicyclopentadienyloxyethyl, bornyl or isobornyl methacrylate, cyclohexyl methacrylate, ethylhexyl mathacrylate, etc. It may be desirable to dilute the non-volatile monomer with methyl methacrylate.

Preferred monomers are monomethacrylates because of the better storage stability of such liquids when dissolved in HV-EBA solutions. It is fully realized that the strength of restoratives containing dimethacrylate ingredients is higher than that of monomethacrylates, but the greater storage stability of the former fully compensates for the increased strength of the latter ingredients.

A ratio of not more than one part of HV-EBA liquid to monomer and one part of ZnO-Al$_2$O$_3$-hydrogenated rosin powder to one part of silanized glass is preferred. Although cements with better mechanical properties are obtained with higher ratios of monomer and reinforcing agent, the biocompatibility, such as pulp irritation, is generally better for the former formulations. These types of restoratives are primarily employed because of their excellent compatibility to dental tissues. Thus the biocompatible properties are more important characteristics of these cement-composites than mechanical strength.

Cement-composites using such compositions have compressive strength of one and a half to three times those of reinforced ZOE cements and many times the strength of unreinforced ZOE materials. They have much lower solubility than ZOE cements and do not inhibit polymerization of dental resins or composites.

These cement-composites, unlike ZOE cements, adhere strongly to many substrates such as stainless steel, composites or porcelain, even in the aqueous environment encountered in the mouth. Rupture occurs due to cohesive failure and approximates the tensile strength of the material.

In addition, storage stability of the preferred composition is excellent and allows a long shelf-life of the ingredients. Moreover, the compositions described yield a strong, insoluble, biocompatible material suitable as an intermediate restorative resin and as a restorative in the repair of fractured porcelain or porcelain to metal crown and bridges.

EXAMPLE 5

Sources of monomers, initiators, accelerators and other chemicals employed in this example are given in Table 4. The powders were sieved and mixed as previously described. The desired amount of silanized glass coated with benzoyl peroxide was then incorporated into the powder. Setting time, compressive strength, solubility and disintegration were determined according to the respective tests of ANSI/ADA Specification No. 30 for Dental Zinc Oxide-Eugenol Type Restorative Materials. Diametral tensile strength was determined with a universal testing machine at a loading rate of 0.5 cm/min. The technique for measuring bond strength of the cements to composites or non-precious metal is the same as that described above.

Powders were silanized by the following procedure. A 3 g sample of the powder (glass, fumed silica, zinc oxide or aluminum oxide) was mixed with 80 ml cyclohexane, 0.06 g n-propylamine and 0.06 g 3-methacryloxypropyltrimethoxysilane. The flask containing the mixture was connected to a rotary evaporator and a slight vacuum was applied for 1 to 2 hrs. The vacuum and the temperature of the surrounding water bath were increased until the temperature of the bath reached 60° C. After 3 to 4 hrs. at this temperature the contents of the flask were removed. The material was pulverized and placed back into the flask under a vacuum until all solvent had been removed.

Accelerated aging tests of the liquid ingredients of the cement were conducted in a 45° C. oven. Formation of solid polymer on storage at this temperature was observed by visual observation of the specimens at successive time intervals.

TABLE 4

| Source of Materials | |
|---|---|
| | Source |
| Monomers | |
| methyl methacrylate, inhibited with 65 ppm hydroquinone monomethyl ether | Aldrich Chemical Co. Milwaukee, WI |
| cyclohexyl methacrylate | Monomer-Polymer Laboratories Philadelphia, PA |
| isobornyl methacrylate | Polysciences, Inc. Warrington, PA |
| dicyclopentenyloxyethyl methacrylate inhibited with 50 ppm hydroquinone | Rohm and Hass Philadelphia, PA |
| 1,10-decamethylene glycol dimethacrylate | Esschem . / Essington, PA |
| Other Chemicals | |
| n-hexyl vanillate | synthesized |
| 4-N,N—diethylaminophenylacetic acid | " |
| 4-N,N—diethylaminophenylacetic acid ethyl ester | " |
| 2,6-di-tert-butyl-4-hydroxytoluene (BHT, Tenox ®) | Tennessee Eastman Kingsport, TN |
| 3-methacryloxypropyltrimethoxysilane (A-174) | Union Carbide New York, NY |

TABLE 4-continued

Source of Materials

| | Source |
|---|---|
| zinc oxide | Mallinckrodt Company St. Louis, MO |
| Aluminum oxide T-61 and T-61-325 tabular alumina | Alcoa Chemicals Bauxite, AR |
| hydrogenated rosin (Staybelite) | Hercules, Inc. Wilmington, DE |
| barium fluoride containing glass (Corning glass No. 7724) | Corning Glass Corning, NY |
| high surface area silica (Cab-O-Sil M-5) | Godfrey L. Cabot, Inc. Boston, MA |

All other chemicals were reagent grade.

TABLE 5

Properties of Intermediate Restorative Materials

Powder: 1 part: 64% ZnO - 30% $Al_2O_3$ - 6% hydrogenated rosin
1 part: silanized glass + 1% benzoyl peroxide
Liquid: 1 part: 12.5% hexyl vanillate - 87.5% EBA
1 part monomer + 1% N,N—dihydroxyethyl-p-toluidine + 0.02% BHT
Powder/liquid ratio: 1.8 g/0.2 ml

| Percent of Monomer in Liquid | Setting Time min. | Strength, MPa* Compressive | Tensile | Solubility % | Adhesion Composite | MPa to St. Stet. |
|---|---|---|---|---|---|---|
| Methyl methacrylate (MMA) | 6 | 111.7 (20.6) | 10.4 (0.7) | 0.17 | 10.3 ± 2.6 | 9.8 ± 1.3 |
| Methyl methacrylate+ | 6 | 107.9 (5.2) | 12.3 (0.3) | — | — | — |
| QM-657++ | 8 | 104.3 (8.6) | 13.2 (1.7) | 0.24 | 7.0 ± 2.2 | 11.7 ± 1.0 |
| 65% dichlopentyl methacrylate + 35% MMA§ | 7 | 100.2 (10.3) | 12.5 (2.1) | — | — | — |
| 95% diclopentenyl methacrylate + 5% MMA | 6.5 | 99.1 (17.3) | — | — | — | — |
| Isobornyl Methacrylate | 8 | 105.3 (6.0) | 15.2 (0.2) | — | — | — |
| Cyclohexyl Methacrylate | 8.5 | 104.7 (8.6) | 15.8 (2.0) | 0.34 | 4.1 ± 2.4 | 15.1 ± 1.8 |
| 70% Cyclohexyl methacrylate + 30% MMA | 8.5 | 78.1 (9.1) | 13.2 (1.7) | 0.53 | 7.3 ± 1.6 | 15.6 ± 3.2 |
| Commercial intermediate restorative (IRM) | 7.5 | 62 | 5.2 (0.4) | 1.11 | 0.1 ± 0.1 | 1.1 ± 0.2 |

*Average of 5 measurements ± standard deviation of 5 measurements
+Substituted 1% N,N—dimethylaminophenethanol for the 1% dihydroxyethyl-p-toluidine
++Dicyclopentenyloxyethyl methacrylate
§Powder-liquid ratio 1.64/0.2 ml

TABLE 6

Properties of Intermediate Restorative Materials with QM-657 and Methyl Methacrylate Monomers as Ingredients Composition:
Powder: $I_1$: 64% ZnO - 30% $Al_2O_3$ - 6% hydrogenated rosin
$I_2$: silanized glass coated with 1% benzoyl peroxide
Liquid: $I_3$: 12.5% n-hexyl vanillate - 87.5% EBA
$I_4$: 70% dicyclopentenyloxyethyl methacrylate (QM-657) + 30% methyl methacrylate (MMA) + 1% dihydroxyethyl-p-toluidine (DHEPT) + 0.02% BHT

| Composition, Parts by weight | | | | Powder/ Liquid Ratio | Setting Time | Strength,* MPa | | Percent | Adhesion* (MPa) to: | |
|---|---|---|---|---|---|---|---|---|---|---|
| Powder | | Liquid | | | | | | | | |
| $I_1$ | $I_2$ | $I_3$ | $I_4$ | g/0.2 ml | min | Compressive | Tensile | Solubility | Composite | Stainless Steel |
| 1 | 1 | 1 | 1+ | 1.8 | 8 | 104.3 (8.6) | 13.2 (1.7) | 0.24 | 7.0+ (2.2) | 11.7 (0.1) |
| 1 | 1 | 1 | 1 | 1.8 | 6.5 | 111.7 (13.2) | 13.4 (0.5) | 0.46 | 6.4 (0.9) | 12.4 (1.3) |
| 1 | 1 | 1 | 1 | 1.8+ | 5 | 103.8 (6.2) | 10.2 (1.4) | — | — | — |
| 1 | 1 | 1 | 1 | 2.2 | 7.5 | 94.1 (2.8) | 14.7 (1.7) | 0.56 | 7.9• (1.0) | 14.5• (1.5) |
| 1 | 1 | 1 | 1 | 1.8 | 5 | 98.2 (5.2) | 12.3 (1.9) | 0.23 | — | — |
| 1 | 1 | 1 | 1 | 1.8 | 5 | 98.0 (14.3) | 12.6 (1.6) | 0.42 | 6.0 (0.9) | 10.7 (1.3) |
| 1.5 | 1 | 1 | 1.5 | 2.0 | 7.5 | 72.6 (7.1) | 10.1 (1.6) | — | 8.9# (0.2) | 11.5# (1.6) |
| 1 | 1.5 | 1 | 1 | 1.8 | 6 | 102.8 (8.1) | 12.1 (2.3) | — | 8.4 (2.2) | 7.4 (1.5) |
| 1 | 1.5 | 1 | 1.5 | 1.67 | 6.5 | 73.3 (7.5) | 11.1 (2.1) | — | 9.9# (1.5) | 8.4# (0.2) |
| 1 | 1 | 1 | 1 | 1.8⁻ | 7.5 | 108.4 (4.3) | 10.0 (0.7) | 0.60 | 5.2 (0.7) | 9.7 (0.7) |
| Commercial composite (IRM) | | | | | 7.5 | 62 | 5.2 (0.4) | 1.1 | 0.1 (0.1) | 1.1 (0.2) |

*average of 5 measurements with standard deviation in parentheses
+$I_4$ = 100% QM 657 + 1% DHEPT + 0.02% BHT
  plus 0.1% methacrylic acid
  plus 0.2% methacrylic acid
  plus 1% methacrylic acid
  $I_4$ = 72% QM-657 − 28% MMA + 1% DHEPT + 0.02% BHT + 10% methacrylic acid
⁻50% QM-657 − 50% MMA + 1% DHEPT + 0.02% BHT
•powder-liquid ratio of mix: 2.0 g/0.2 mL
powder-liquid ratio of mix: 1.7 g/0.2 mL

TABLE 7

Effect of Silanization of Powder on the Physical Properties of Restorative Cements Powder (1 part): 64% ZnO - 30% $Al_2O_3$ - 6% hydrogenated rosin ($I_1$)
silanized glass with 1% benzoyl peroxide ($I_2$)

Liquid (1 part): 12.5% hexyl vanillate - 87.5% EBA ($I_3$)
70% QM-657 - 30% methyl methacrylate + 1% N,N—dihydroxy-ethyl-p-toluidine + 0.02% BHT ($I_4$)

| Variation in Composition of Powder ($I_1 + I_2$) | Powder Liquid Ratio g/0.2 mL | Setting Time min. | Strength, MPa* Compressive | Tensile | Comments |
|---|---|---|---|---|---|
| None | 1.8 | 8 | 104.3 (8.6) | 13.2 (1.7) | |
| 0.25% silanized silica added+ | 1.6 | 5.5 | 101.7 (3.5) | 10.7 (1.3) | difficult to mix |
| 0.5% silanized silica added+ | 1.6 | 5.5 | 98.8 (4.5) | — | |
| 0.5% silanized silica added+ | 1.8 | 5.5 | 105.3 (4.7) | — | difficult to mix |
| 1.0% silanized silica added+ | 1.8 | 5.5 | 98.8 (2.4) | — | difficult to mix |
| 1.0% silanized silica added | 1.8 | 5 | 105.0 (7.1) | — | difficult to mix |
| $I_2$ with 10% silanized ZnO | 1.8 | 6 | 82.7 (4.1) | — | — |
| $I_1$ with 8% silanized ZnO | 1.8 | 9 | 101.8 (6.7) | 10.2 (0.3) | — |
| $I_1$ with 16% silanized ZnO | 1.8 | 9 | 93.0 (7.7) | — | — |
| $I_1$ with 15% silanized $Al_2O_3$ | 1.8 | 8 | 80.0 (6.1) | — | — |
| $I_1$ with 5% silanized $Al_2O_3$ | 1.8 | 10 | 102.6 (6.2) | 10.0 (0.8) | — |

*Average of 5 measurements ± standard deviation
+Cab-O-Sil M-5
$I_4$ + 1% methacrylic acid

TABLE 8

Properties of n-Hexyl Vanillate-EBA Polymer Cement-Composites

Ingredients:
Powder: $I_1$: 64% ZnO - 30% $Al_2O_3$ - 6% hydrogenated rosin
$I_2$: silanized glass coated with 1% benzoyl peroxide
Liquid: $I_3$: 12.5% n-hexyl vanillate - 87.5% EBA
$I_4$: 1,10-decamethylene dimethacrylate (DMDMA) + 1% N,N—diethylaminophenylacetic acid (DEAPAA) + 0.02% butylated hydroxytoluene (BHT)
Powder/Liquid ratio: 1.8 g/0.2 ml

| Composition | | | | Setting Time | Strength* | |
|---|---|---|---|---|---|---|
| Powder+ | | Liquid+ | | | Compressive | Tensile |
| $I_1$ | $I_2$ | $I_3$ | $I_4$ | min | MPa | MPa |
| 2 | 1 | 1 | 1 | 7.5 | 137.6 (5.8) | — |
| 2 | 1 | 1 | 1 | 9 | 127.9 (7.1) | 15.7 (1.4) |
| 2 | 1 | 2 | 1 | 7.5 | 109.9 (8.0) | 10.7 (2.6) |
| 2 | 1 | 1 | — | 9 | 49.9 (2.9) | 8.0 (1.3) |
| 1 | 1 | 2 | 1 | 7 | 118.1 (6.3) | 11.8 (1.8) |
| 1 | 1 | 1 | 1⁻ | 7 | 127.0 (4.4) | 18.0 (1.9) |
| 1 | 1 | 1 | 1 | 10 | 131.9 (7.2) | 13.0 (0.8) |
| 1 | 1 | 1 | 2# | 6 | 177.9 (1.0) | 15.9 (0.8) |
| 1 | 1.5 | 1 | 1# | 9.5 | 150.1 (4.8) | 14.3 (3.8) |
| 1 | 1.5 | 2 | 1 | 5.0 | 132.8 (6.9) | 15.6 (0.9) |
| 1 | 2 | 1 | 2# | 4.5 | ~199 | — |
| 1 | 2 | 2 | 1# | 5.0 | 136.3 (4.8) | 17.1 (3.0) |
| ZOE cement | | | | 4–10 | 28–61 | 1.4–5.2 |

*Average of 5 determinations ± standard deviation
+Parts by weight
DMDMA + 0.5% N,N—dimethylaminophenylacetic acid
DMDMA + 0.5% DEAPAA + 0.05% BHT
Unsilanized glass
Powder/liquid ratio 1.3 g/0.2 ml
⁻DMDMA + 0.5% DEAPAA + 0.04% BHT
5% BIS-GMA added
Slurry difficulty to mix The properties of cement composites prepared with monomethacrylates are given in Tables 5-7 and with dimethacrylates are given in Table 8.

The powder-liquid ratio to obtain a standard consistency varied somewhat with the type of aluminum oxide. Compositions containing aluminum oxide (T-61-325) had improved mixing properties, a slightly higher powder-liquid ratio and minor increases in compressive strength compared with those using aluminum oxide (T-61). Setting times decreased by 1 min. when the EBA in the mix had been stored for a number of years.

Compressive strength values appeared to be affected by the batch of zinc oxide used.

Intermediate restoratives prepared from 1 part 64% ZnO—30% $Al_2O_3$ and 6% hydrogenated rosin and 1 part silanized glass coated with 1% benzoyl peroxide powder and a liquid consisting of 1 part 12.5% hexyl vanillate—87.5% EBA and 1 part monomer and 1% N,N-dihydroxyethyl-p-toluidine plus 0.02% BHT inhibitor hardened in 6 to 8.5 min. (Table 5). With methyl methacrylate monomer, cement-composites having good compressive and tensile strengths were obtained. Thus, the strength of the intermediate restorative resin was much higher than that of presently available commercial resins.

Since methyl methacrylate is quite volatile, loss of monomer occurs on mixing which sometimes resulted in incomplete wetting of the powder. To overcome this deficiency dicyclopentenyloxyethyl methacrylate (QM-657) a high molecular weight monomer was substituted for methyl methacrylate. Cements with QM-657 cured in 8 min. and had physical properties similar to materials containing methyl methacrylate. Cements containing the slightly colored but less viscous dicyclopentenyl methacrylate and methyl methacrylate had characteristics similar to those having QM-657 as an ingredient. Highest tensile strengths (15.2 MPa) were obtained with cements with isobornyl methacrylate and cyclohexyl methacrylate, respectively. However, the HV-EBA isobornyl methacrylate-amine-BHT liquid partially polymerized in 24 hrs. on storage at 45° C. Cements with QM-657 or cyclohexyl methacrylate as monomer had the most desirable overall properties.

Table 6 gives values of the physical properties of cement-composites prepared with QM-657 diluted with methyl methacrylate. All materials hardened in 5 to 8 mins. Compressive strength was over 50% higher and the tensile strength two and a half times that of commercial intermediate restorative materials. Solubility varied from 0.23 to 0.60%. Especially noteworthy was the excellent adhesion of all formulations both to composites and stainless steel with maximum adhesive tensile strength of the cement to these substrates of 9.9 MPa and 14.5 MPa respectively. Bond failure always occurred within the restorative material.

Properties of a cement composite in which the various powder ingredients besides the glass component had been silanized are given in Table 7. Neither addition of from 0.5% to 2% fumes silica, silanization of a portion of the zinc oxide or aluminum oxide improved the strength. Incorporation of fused silica reduced the workability of the mix, but speeded up the setting time. Thus, silanization of the glass alone improved the strength of the restorative material.

Substitution of a dimethacrylate such as 1,10-decamethylene dimethacrylate for the monomethacrylate in the liquid yielded cements with properties described in Table 8. Mixes with good working properties could be obtained that, depending on the ratio of the zinc oxide to glass powder and that of HV-EBA to dimethacrylate liquid, gave setting times ranging from 4.5 to 10 mins. Powders containing a high proportion of the silanized glass component and/or liquids with a high percentage of the monomer ingredient cured fastest, possibly because of the more rapid polymerization of the latter in the presence of higher concentrations of initiator and accelerator. As expected, mechanical properties of the cement were increased by the incorporation of larger concentrations of the dimethacrylates and glass ingredients into the mix. Inspection of the results given in Table 6 also lead to the following conclusions: (1) too high a proportion of glass in the mix decreases the working properties of the cement, (2) silanization of the glass greatly improves strength, (3) compressive and tensile strength were higher for cements with dimethacrylate ingredients than for those containing monomethacrylate monomers (Table 4), (4) with increasing concentration of dimethacrylate the compressive strength rose from 110 to 199 MPa, (5) tensile strength was less dependent on monomer content and varied from 11.8 to 18.0 MPa. Thus, these materials had compressive and tensile strengths two to three times those of reinforced ZOE cements, (7) addition of 5% BIS-GMA [isopropylidene bis(p-phenoxy [2-hydroxytrimethylene]) dimethacrylate] with the dimethacrylate did not improve the characteristics of the cement. The storage stability of the combined hexyl vanillate-EBA-dimethacrylate-amine accelerator liquid was not as great as would be desired.

Results of accelerated aging tests of cement liquids of various compositions are given in Table 9. The n-hexyl vanillate-EBA solutions were very stable and could be stored at 45° C. for years. The mono- or dimethacrylates with tertiary amines and BHT inhibitor were stable on storage at 45° C. for at least 1.5 years. However, acids such as EBA when dissolved in a typical dimethacrylate (1,10-decamethylene dimethacrylate) in the presence of a tertiary amine lead rapidly, often within a few hours, to the partial polymerization of the monomer. The neutral N,N-dihydroxyethyl-p-toluidine or N,N-diethylaminophenylacetic acid ethyl ester accelerators imparted considerably longer storage stability, ranging from 10 to 15 days, to the dimethacrylate-HV-EBA solution than N,N-diethylamino-phenethanol or N,N-dialkylaminophenylacetic acids.

TABLE 9

Storage Stability of Cement Liquids at 45° C.

| Composition of Liquids: (prepared from equal parts, by weight) | | Storage Stability of Combined |
|---|---|---|
| Part A | Part B | Liquid at 45° C. |
| EBA | Decamethylene dimethacrylate | 17 days |
| " | Decamethylene dimethacrylate + 1% DEAPAA* | 1.5 hr |
| n-Hexyl vanillate (HV) | " | 60 days |
| none | Decamethylene dimethacrylate + 1% DEAPAA* + 0.02% BHT+ | 500+ days |
| 12.5% HV — 87.5% EBA | none | 900+ days |
| " | Decamethylene dimethacrylate + 1% DEAPAA + 0.02% BHT | 3 hr |
| " | Decamethylene dimethacrylate + 1% DEAPAA + 0.08% BHT | 3 hr |
| " | Decamethylene dimethacrylate + 1% DEAPE + 0.02% BHT | 1 hr |
| " | Decamethylene dimethacrylate + 1% DHAFA + 0.02% BHT | 2.5 days |
| " | Decamethylene dimethacrylate + 1% DHEPT + 0.1% BHT | 10 days |
| " | Decamethylene dimethacrylate + 1% DEAPAA-EE + 0.1% BHT | 15 days |
| " | Methyl methacrylate (MMA) + 1% DHEPT + 0.02% BHT | 500+ days |
| " | Methyl methacrylate (MMA) + 1% DEAPAA + 0.02% BHT | 500+ days |
| " | Methyl methacrylate (MMA) + 1% DEAPAA-EE + 0.02% BHT | ~180 days |
| " | 70% cyclohexyl methacrylate + 30% MMA + 1% DHEPT + 0.02% BHT | 200+ days |
| " | QM 657⁻ + 1% DHEPT + 0.02% BHT | ~200 days |
| " | 70% QM 657⁻ + 30% MMA — 1% DHEPT + 0.02% BHT | ~180 days |

*4-N,N—diethylaminophenylacetic acid
+butylated hydroxytoluene
4-N,N—diethylaminophenethanol
4-N,N—dimethylaminobenzoic acid
4-N,N—dihydroxyethyl-p-toluidine
4-N,N—diethylaminophenylacetic acid ethyl ester
⁻dicyclopentenyloxyethyl methacrylate
time after which solid polymer had precipitated
liquid had darkened Solutions containing monomethacrylates (methyl methacrylate, dicyclopentenyloxyethyl methacrylate, (QM-657), cyclohexyl methacrylate) were much longer stable in a 45° C. environment than dimethacrylates. An HV-EBA solution mixed with methyl methacrylate containing 1% dihydroxyethyl-p-toluidine (or 1% diethylaminophenylacetic acid) and 0.02% BHT did not polymerize within the 500 day observation period. With QM-657 as monomer the solutions hardened after 0.5 years.

The compatibility of HV-EBA-ZnO cements with acrylic monomers permits the formulations of the newly developed intermediate restorative resins. The cured "cement-composites" harden within a few minutes, that is a time interval satisfactory for clinical applications. Although setting times may vary by ±1 min using different batches of ingredients, such changes can be minimized by careful quality control of the starting materials. The mechanism of hardening appears to involve both formation of a zinc salt or even a chelate and the nearly simultaneous polymerization of the monomer as a result of the initiator-accelerator system present in the mix.

Enhancement of the physical properties of the cement by addition of monomer and glass may result from the establishment of an interpenetrating network of the cement embedded in the glass reinforced resin. The improved packing of the cement and better matrix adhesion to residual powder and resin particles may also contribute to the increase in mechanical properties.

Variations in compressive strength were observed with different batches of ingredients. Thus, careful quality control of raw materials is required. Greatest strength was obtained with compositions containing a high percentage of monomer and glass. Strength of the most useful compositions is much superior to that of presently available intermediate restorative resins with the increase in compressive strength ranging from 40% to over 100% and a 200% to 300% improvement in tensile strength. The excellent biocompatibility of the monomer-free cement may be reduced by the addition of methacrylate or glass, especially in high concentrations. Efforts in this study were therefore directed to optimize properties of formulations containing not more than equal parts of the resin and cement components.

Dimethacrylate monomers yield stronger cements than those prepared with monomethacrylate ingredients. However, when dissolved in hexyl vanillate, EBA and amine, the dimethacrylates have poor storage stability and partially polymerize at room temperature within days. Separate storage of the HV-EBA and the inhibited dimethacrylate and accelerator prior to mixing the ingredients overcomes this problem.

Cements-composites with the best overall characteristics have been obtained with monomethacrylates. The commercialization of a clinically useful product requires a long shelf life of its ingredients. Therefore, somewhat lower strength is compensated for by the much improved storage stability. Methyl methacrylate is too volatile and when used as cement ingredient may yield dry mixes in which a portion of the powder does not form a cohesive mass. Cements incorporating dicyclopentadienyloxyethyl methacrylate (QM-657) either as the only monomeric ingredient or partially diluted with methyl methacrylate have excellent properties. A 70% QM-657, 30% methyl methacrylate (by weight) solution to which HV-EBA has been added mixes well with the powder and yields cements with strength not attainable with similar intermediate restoratives. Excellent properties, especially tensile strength are also obtained on using cyclohexyl methacrylate as monomer.

A big advantage of the cement-composites over the commercial intermediate restoratives which have minimal adhesion is their excellent bonding to various substrates even in an aqueous environment. Tensile strength of the cement-substrate bond reaches as high as 9.9 MPa (1435 psi) to composites and 15.6 MPa (2262 psi) to stainless steel. Failure occurs cohesively within the material in the range of the tensile strength of the intermediate restorative cement-composite. This strong adhesion may have clinical applications in the repair of fractured porcelain or porcelain to metal crown and bridges, to which the cement strongly adheres.

No adhesion of the material to untreated enamel or dentin has been observed in the presence of water. Using HV-EBA-ZnO cement significant adhesion of stainless steel to acid etched enamel has been obtained. Future studies should establish if on pretreatment of dentinal surfaces the cement bonds to this substrate. The HV-EBA-ZnO cement illicits pulp reactions similar to intermediate restoratives based on eugenol. The most promising properties for cement-composite restorations were obtained with solutions containing the high molecular weight, commercially available dicyclopentenyloxyethyl methacrylate (QM-657)

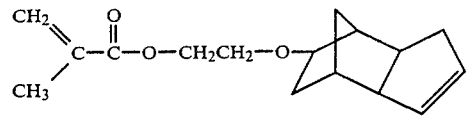

without or with and methyl methacrylate as diluent or cyclohexyl methacrylates as monomers. The former monomer according to the manufacturer's fact sheet has low volatility, low odor, low viscosity, low curing shrinkage and is non-mutagenic. Its acute oral toxicity in rats and acute dermal toxicity in rabbits are both greater than 5 g/kg. Acute toxicity screening tests on rabbits are reported to have shown only slight irritation of the eyes and a primary skin irritation index of 2.5. Guinea pigs were not sensitized on exposure.

Hexyl vanillate-EBA-ZnO cements are compatible with acrylic monomers (e.g. dicyclopentenyloxyethyl methacrylate, cyclohexyl methacrylate). Such solutions mixed with powder, made up from silanized glass reinforcing agent and zinc oxide and containing suitable initiatoraccelerator systems, have good working properties and harden in a few minutes. The cured materials have compressive and tensile strength one and a half to three times that of eugenol based intermediate restoratives. These cement-composites adhere strongly to composites, non-precious metals or porcelain. Rupture of the bond occurs as the result of cohesive failure.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In a cementitious dental composition comprising a solid phase which includes a metal oxide or hydroxide of a Group II metal or tin and a liquid phase which includes a chelating compound, said chelating compound comprising an ester containing at least one vanillyl group, said ester being the product of a reaction of an alcohol and at least one of a member selected from the group consisting of vanillic acid, isomers of vanillic acid, and homologs of vanillic acid, or other molecules containing vanillyl groups, the improvement comprising a syringic acid ester in an amount sufficient to inhibit caries formation.

2. The cementitious dental composition of claim 1, further comprising a solvent.

3. The cementitious dental composition of claim 1, further comprising a silanized glass powder as filler.

4. The cementitious dental composition of claim 1, wherein the alcohol moiety of the syringic acid ester is n-hexyl or 2-ethylhexyl.

5. The cementitious dental composition of claim 2, wherein said solvent is a chelating agent.

6. The cementitious dental composition of claim 5, wherein said chelating agent is o-ethoxybenzoic acid.

7. The cementitious dental composition of claim 2, further comprising a liquid vanillate ester which serves as said solvent and as said ester of the vanillic acid moiety.

8. The cementitious dental composition of claim 1, wherein said liquid phase consists essentially of about 5% to ethylhexyl syringate, about 7% n-hexyl vanillate and about 88% o-ethoxybenzoic acid.

9. The cementitious dental composition of claim 1, wherein said composition further comprises a polymer.

10. The cementitious dental composition of claim 9, wherein said polymer is present in said composition in an amount between 1 and 20% by weight, based on the weight of said composition.

11. The cementitious dental composition of claim 1, wherein said composition additionally contains a monomer polymerizable by a free radical mechanism, a polymerization initiator and accelerator.

12. The cementitious dental composition of claim 3, wherein said liquid phase further comprises o-ethoxybenzoic acid, an inhibited methacrylate monomer, an initiator and accelerator, and said solid phase comprises a powder containing zinc oxide and aluminum oxide and hydrogenated rosin.

13. The cementitious dental composition of claim 12, wherein said inhibited methacrylate monomer is a mono-methacrylate.

14. The cementitious dental composition of claim 12, wherein said inhibited methacrylate monomer comprises a high molecular weight monomer of low volitility.

15. The cementitious dental composition of claim 12, wherein said liquid phase comprises up to one part of mixture of said vanillate ester with said o-ethoxybenzoic acid to one part of said inhibited methacrylate monomer; and said solid phase comprises approximately one part of a mixture of said zinc oxide with said aluminum oxide and said hydrogenated rosin, to one part of said silanized glass powder.

16. The cementitious dental composition of claim 14 wherein said inhibited methacrylate monomer is cyclohexyl methacrylate or dicyclopentenyloxyethyl methacrylate with or without a monomeric diluent.

17. The cementitious dental composition of claim 12 wherein said accelerator is a tertiary aromatic amine containing no acetic groups such as N,N-dihydroxyethyl-p-toluidine or a dialkylaminophenylacetic acid ester.

18. The cementitious dental composition of claim 1, wherein said liquid phase contains about 10-30% n-hexyl syringate and about 90-70% o-ethoxybenzoic acid.

19. A restored dental element comprised of porcelain or porcelain to metal cemented together by the composition of claim 1.

20. A cementitious dental composition comprising a solid phase which includes a metal oxide or hydroxide of a Group II metal or tin and a liquid phase which includes a chelating compound, said chelating compound comprising a syringic acid ester in an amount sufficient to inhibit caries formation.

21. The cementitious dental composition of claim 20, further comprising a silanized glass powder as filler.

22. The cementitious dental composition of claim 20, wherein said composition further comprises a polymer.

23. The cementitious dental composition of claim 22, wherein said polymer is present in said composition in an amount between 1 and 20% by weight, based on the weight of said composition.

24. The cementitious dental composition of claim 20, wherein said composition additionally contains a monomer polymerizable by a free radical mechanism, a polymerization initiator and accelerator.

25. The cementitious dental composition of claim 20, wherein said liquid phase consists essentially of about 10-30% n-hexyl syringate and about 90-70% o-ethoxybenzoic acid.

26. A restored dental element of porcelain or porcelain to metal cemented together by the composition of claim 20.

* * * * *